(12) United States Patent
Murata et al.

(10) Patent No.: US 6,251,355 B1
(45) Date of Patent: Jun. 26, 2001

(54) FINE CISPLATIN POWDER AND PROCESS FOR THE PRODUCTION THEREOF

(75) Inventors: Toshitaka Murata; Keizou Ishikawa, both of Saitama; Osamu Kogawa, Chiba; Kenji Iwata, Saitama, all of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/319,837

(22) PCT Filed: Dec. 22, 1997

(86) PCT No.: PCT/JP97/04747

§ 371 Date: Jun. 10, 1999

§ 102(e) Date: Jun. 10, 1999

(87) PCT Pub. No.: WO98/29344

PCT Pub. Date: Jul. 9, 1998

(30) Foreign Application Priority Data

Dec. 25, 1996  (JP) .................................................... 8-355879

(51) Int. Cl.[7] .................................................... C01B 21/00
(52) U.S. Cl. ............................................ 423/413; 424/649
(58) Field of Search ................................................ 423/413

(56) References Cited

U.S. PATENT DOCUMENTS

| 4,302,446 | 11/1981 | Kaplan et al. ........................ 424/131 |
| 4,332,780 | * 6/1982 | Rhoda et al. ........................ 423/413 |
| 4,335,087 | * 6/1982 | Rhoda ................................. 423/413 |

FOREIGN PATENT DOCUMENTS

| 268867 | * 6/1989 | (DE) .................................... 423/413 |
| 62-10930 | 3/1987 | (JP) . |
| 3-13174 | 2/1991 | (JP) . |

* cited by examiner

*Primary Examiner*—Wayne Langel
(74) *Attorney, Agent, or Firm*—Nields & Lemack

(57) ABSTRACT

The present invention relates to a novel fine cisplatin powder utilized as an anticancer agent. The fine cisplatin powder obtained in the present invention does not cause secondary agglomeration, is excellent in fluidity and easily handleable in the pharmaceutical preparation step. Furthermore, the fine cisplatin powder is reduced in the content of N,N-dimethylformamide as the residual solvent, and can be dissolved rapidly in physiological saline, thus being suitable for cancer therapy particularly by intra-arterial injection. This fine powder can be produced by contriving specified means for crystallizing cisplatin from a solution thereof in N,N-dimethylformamide.

5 Claims, 2 Drawing Sheets

FINE CISPLATIN POWDER AND PROCESS FOR THE PRODUCTION THEREOF

TECHNICAL FIELD

The present invention relates to a fine cisplatin powder which can be used in cancer therapy particularly by hepatic intra-arterial injection etc.

BACKGROUND ART

Cisplatin whose antitumor effect was reported in 1969 by Rosenberg (Nature, 222, 385 (1969)) is a typical drug of an antitumor platinum complex developed as an anticancer agent and has an effect on a wide range of cancers such as bladder cancer, testicular tumor, esophageal carcinoma, ovarian cancer, lung cancer etc. Cisplatin is a yellow, odorless crystalline powder and is manufactured into a pharmaceutical preparation in the dosage form of solution mainly as an injection for intravenous infusion.

As cancer therapy is developed, the method of using an anticancer agent becomes diversified. It is said that hepatic carcinoma is a hardly remediable cancer, and that hepatic arterial embolization therapy, chemotherapy such as hepatic intra-arterial injection chemotherapy, general administration chemotherapy etc. plays a certain role for multidisciplinary treatment. In particular, hepatic intra-arterial injection chemotherapy which permits a drug to reach cancer tissues at high concentration is effective. Cisplatin is recognized as a highly effective anticancer agent, and is also expected to use for treatment of hepatic carcinoma. However, the solubility of cisplatin in water is as extremely low as about 1 mg/ml at room temperature, so a commercial injection thereof (0.5 mg/ml) is a dilute solution, thus disadvantageously requiring a too much volume for hepatic intra-arterial injection. Hence, a highly convenient powdered preparation capable of forming a solution at high concentration and usable in hepatic intra-arterial injection chemotherapy has been desired.

Methods for obtaining a fine cisplatin powder are known as disclosed in Japanese Patent Publication Nos. 10930/1987 and 13174/1991 in which cisplatin is dissolved in a tertiary amide or dialkylsulfoxide in which cisplatin can be dissolved, and this solution is mixed with a solvent such as water, alcohol etc. in which cisplatin is insoluble or sparingly soluble, to precipitate fine crystalline cisplatin which is then recovered by filtration.

In the fine cisplatin powder obtained by these methods, however, there remains a tertiary amide etc. used as the solvent at levels as relatively high as 70 ppm or more even in experimental scale, and the residual solvent at levels of 100 ppm or more is inevitable in industrial scale. Accordingly, the contamination of a product with the solvent is inevitable if these methods are used as such. In intra-arterial injection therapy, because a solution containing a medicine at high concentration is directly introduced into a topical affected part, so the effect of impurities should be taken into consideration more than in a conventional pharmaceutical preparation for intravenous injection. The adverse effect of the tertiary amide etc. on the human body is conceivable, and it is desired to remove these impurities at the maximum degree.

Further, the powder according to the conventional methods is a massive material after dried, and the step of disintegrating the massive material by grinding or screening is necessary. Because the bulk material contains 80% or more fine powder with a size of less than 5 $\mu$m, substantially 90% or more, the fine powder will be scattered in the handling thereof in the step of disintegrating the bulk material and in the later step of pharmaceutical manufacturing, so the pollution of the working environment is a problem. In particular, mutagenic anticancer agents such as cisplatin should carefully be handled, and from the problem of powder scattering, the operation in a dry process or in an open system should be avoided. Further, the conventional fine powder is highly agglomerable due to its small size, and thus powder particles are aggregated to form a powder with low fluidity and easily adhere to instruments etc., and the powder is not removed even by movement, thus making its handling difficult in the operation of pharmaceutical manufacturing. These secondarily agglomerated particles have been agglomerated via relatively strong bonding and are hardly dispersible in preparing a solution, thus preventing rapid dissolution.

As another method of pulverization, there is also known a method in which a cisplatin injection is lyophilized to give a powdered medicine. This method is easy in the sterilization process, and the resulting cisplatin powder has the advantage of rapid dissolution. However, a solution of cisplatin in the production step is a dilute solution as described in Japanese Patent Publication No. 13174/1991. Hence, to obtain a cisplatin powder in an amount suitable for use, a large amount of water should be removed, so the process is costly, time-consuming and thus impractical. Further, hydrogen chloride removed simultaneously during lyophilization causes the problem of corrosion of the system of the lyophilization unit. Further, from the problem of stability of the lyophilized product, its glass vessel should be stored at a refrigeration temperature (N.C.I. pharmaceutical data sheet).

Accordingly, the object of the present invention is to produce a bulk of fine cisplatin powder having a low content of a solvent for crystallization, not forming secondarily agglomerated particles preventing dissolution and the operation of pharmaceutical manufacturing, and having higher fluidity as a powder, as well as to provide a pharmaceutical preparation thereof excellent in stability.

DISCLOSURE OF THE INVENTION

The present inventors found that a fine cisplatin powder satisfying said object having high fluidity and hardly causing adhesion and agglomeration can be obtained by dissolving a raw medicine of cisplatin in a solvent such as dimethylformamide etc. containing hydrogen chloride and water, and according to the method of the invention, by precipitating cisplatin crystals. Further, the present inventors found that the resulting fine cisplatin powder is stirred for a predetermined time in a solvent such as dilute hydrochloric acid in which cisplatin is sparingly soluble and the residual solvent is eluted whereby the solvent such as DMF can be sufficiently removed, and also that even after this step of removing the residual solvent, the properties of the fine cisplatin powder obtained in the present invention are maintained so that it remains highly fluidic and hardly causes adhesion and agglomeration, and the present invention is thereby completed.

Further, the amount of the residual solvent in the fine cisplatin powder according to the present invention is considerably lower than those obtained by the prior art methods, and if DMF was used, its content was 60 ppm or less in analysis by gas chromatography. Further, the fine cisplatin powder of the invention is easily dispersed in water or physiological saline to be rapidly dissolved therein by slight shaking at 2 to 3 r.p.s. at room temperature. The raw medicine obtained after drying is highly fluidic powder which does not form secondarily agglomerated particles, thus eliminating procedures such as grinding, and there is no problem with powder scattering and adhesion, so the powder can be easily handled in the operation of pharmaceutical manufacturing. Further, aseptic techniques can be used for production of a sterile raw medicine, and it can be transferred as such to the operation of pharmaceutical manufacturing, thus enabling actual industrial application. The pharmaceutical preparation produced aseptically in this manner can be used as an anticancer agent for intra-arterial injection therapy.

Further, the pharmaceutical preparation of the fine powder of the invention possesses excellent stability and is suspended in distilled water for injection, physiological saline etc. so that it can be used as a pharmaceutical preparation for hepatic arterial embolization therapy.

That is, the present invention relates to the following 1 to 6:

1. A fine cisplatin powder consisting substantially of a fine cisplatin powder passing through a 40-mesh screen, wherein when a fine powder consisting of these finely divided particles is placed on a 40-mesh screen and subjected to a screen passage test (vibration at 50 r.p.s. for 5 minutes with a vibration strength of 4.6 G), the percentage of the secondarily agglomerated particles remaining on the screen is 10% or less, and the fine powder is in a crystal form having the following characteristic peaks in an X-ray powder diffraction pattern:

| $2\theta$ | Spacing (angstrom) |
|---|---|
| 13.98 | 6.329 |
| 15.1 | 5.862 |
| 16.42 | 5.394 |
| 26.92 | 3.309 |

2. A fine cisplatin powder according to item 1 wherein the degree of compressibility of the powder derived from a tapping test is 45 to 54%, the bulk degree is 0.45 to 0.55, and the content of a tertiary amide is 60 ppm or less.
3. A fine cisplatin powder according to item 1 or 2 wherein the dissolution time is within 10 minutes by slight shaking (2 to 3 r. p. s.) to give an aqueous solution of cisplatin at a concentration of 1 mg/ml.
4. A fine cisplatin powder according to item 3 which is used for intra-arterial injection th erapy or for embolization the rapy in cancer therapy.
5. A process for the production of a fine cisplatin powder, comprising the following successive steps:
   (1) preparing a cisplatin solution containing hydrogen chloride at a concentration of 0.3 to 3% (by weight), water at 4% (by weight) to 15% (by weight) and cisplatin at a concentration of 20 to 40 g/L relative to the whole of a tertiary amide solution,
   (2) dropping said cisplatin solution at a constant rate for 20 to 40 minutes to 1- to 4-fold excess volume of 0.1 to 2 N hydrochloric acid kept cold at 10 to 30° C. under stirring to precipitate a fine cisplatin powder, and
   (3) recovering the precipitated fine cisplatin powder by filtration.
6. A process for the production of a fine cisplatin powder having a reduced content of an organic solvent which comprises suspending and stirring an organic solvent-containing fine cisplatin powder in 0.02 to 1 N hydrochloric acid at room temperature for 1 to 5 hours, then filtering and recovering it.

BEST MODE FOR CARRYING OUT THE INVENTION

Figure 1:
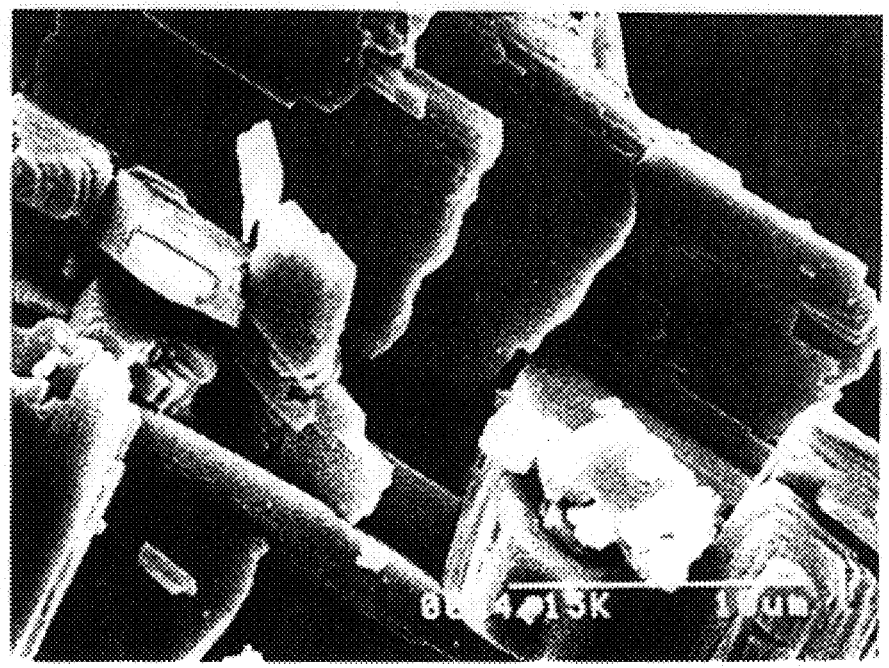
FIG. 1 is an electron microphotograph (4000×) of the fine cisplatin powder according to the present invention.

Hereinafter, preferable conditions are described for a process for producing the fine cisplatin powder of the invention which is highly fluidic and rapidly dissolved.

Cisplatin used as the starting material in the present invention is not particularly limited, and according to a process represented by Indian Journal of Chemistry, Vol. 8, page 193 (1970), cisplatin having purity usable in a raw medicine for pharmaceutical preparations is preferable.

Cisplatin as the starting material is first dissolved in a tertiary amide solution containing hydrogen chloride and water to prepare a cisplatin solution consisting of the tertiary amide solution containing hydrogen chloride at 0.3 to 3% (by weight), water at 4% (by weight) to 15% (by weight) and cisplatin at a concentration of 20 to 40 g/L relative to the whole of the tertiary amide solution. This cisplatin solution may be prepared in any manner, but usually hydrochloric acid is first mixed uniformly with a tertiary amide, and cisplatin is then dissolved in said hydrochloric acid/tertiary amide solution to give the cisplatin solution. That is, cisplatin is dissolved at a concentration of about 20 to 40 g/L in a hydrochloric acid/tertiary amide solution containing hydrogen chloride at about 0.3% (by weight), preferably about 0.4% (by weight) to about 4% (by weight), more preferably about 3% (by weight), water at about 4% (by weight), preferably about 7% (by weight) to about 15% (by weight), more preferably about 12% (by weight) relative to the whole of the tertiary amide solution. The above-mentioned hydrochloric acid/tertiary amide solution for dissolving cisplatin may be prepared in any manner, and usually it can be obtained by adding 2 to 6 N, preferably 2.5 to 4 N hydrochloric acid to a tertiary amide such as dim-ethylformamide (DMF) and mixing them. The amount of hydrochloric acid added is 5 to 15% (by weight), preferably 8 to 12% (by weight) relative to the whole of the resulting solution.

The present inventors found that when the cisplatin solution obtained in the manner described above is dropped into dilute hydrochloric acid to precipitate crystals, the qualities thereof is affected by the time of dropping. That is, when 1 to 4 litters of said cisplatin solution was dropped under stirring into hydrochloric acidwhosevolume is 1- fold to 4-fold excess relative to said cisplatin solution, a fine powder poor in fluidity and easily forming secondarily agglomerated particles was formed if the time of dropping was within 20 minutes, whereas a powder which though excellent in fluidity, is significantly poor in dissolution was formed if the cisplatin solution was dropped for 40 minutes or more. That is, the time of dropping is preferably 20 to 40 minutes, more preferably 22 to 35 minutes.

The temperature for precipitation of crystals is kept cold at 10 to 30° C., preferably 12 to 25° C. It was observed that precipitation of crystals at higher temperature causes a reduction in yield. As described above, the method of adding the cisplatin solution to dilute hydrochloric acid is preferable to precipitate crystals. Although the order of addition in the method may be reversed depending on the case, the method of adding the cisplatin solution to dilute hydrochloric acid as described above is advantageous for the easiness of temperature control. The reaction system is preferably stirred uniformly, but the qualities of the product are less influenced by the stirring speed and the shape of stirring blades.

That is, a preferable process for production of the fine cisplatin powder of the invention comprises:

(1) preparing a cisplatin solution having cisplatin dissolved at a concentration of 20 to 40 g/L preferably 22 to 30 g/L in a tertiary amide solution containing 2 to 6 N preferably 2.5 to 4 N hydrochloric acid in an amount of 5 to 15% preferably 8 to 12%, (2) dropping said cisplatin solution at a constant rate for 20 to 40 minutes, preferably 22 to 35 minutes to 1 to 4-fold excess volume, preferably 1.5 to 3-fold excess volume, of 0.1 to 2 N preferably 0.2 to 0.6 N hydrochloric acid kept at 10 to 30° C. preferably 12 to 25° C. under stirring to precipitate a fine cisplatin powder, and (3) recovering the precipitated fine cisplatin powder by filtration.

The tertiary amide in the present invention includes e.g. N,N-dialkylformamide and N,N-dialkylacetamide. Specific examples thereof include N,N-dimethylformamide, N,N-diethylformamide, N,N-dimethylacetamide, N,N-diethylacetamide etc. In particular, N,N-dimethylformamide is preferable in the present invention.

A fine cisplatin powder from which a crystallizing solvent, for example a tertiary amide has been removed at the maximum degree, is obtained in the following step.

The precipitated fine cisplatin powder is filtered, recovered and suspended in 0.02 to 1 N preferably 0.05 to 0.2 N dilute hydrochloric acid, stirred at room temperature preferably at 10 to 30° C., for 1 hour or more, more preferably 3 hours or more to 5 hours or less, preferably within 4.5 hours, followed by filtration to remove the residual solvent.

According to this step of removing the solvent, the content of the solvent in the fine cisplatin powder of the invention can be reduced to 60 ppm or less, preferably 55 ppm or less, more preferably 40 ppm or less, most preferably 30 ppm or less. The fine cisplatin powder of the invention thus obtained is characterized in that it has a significantly low content of the residual organic solvent (for example, 10 to 60 ppm, preferably 10 to 55 ppm, more preferably 10 to 40 ppm, most preferably 10 to 30 ppm), is excellent in stability during storage and is excellent in fluidity due to hard formation of large secondary aggregate particles.

Hereinafter, the properties of the fine cisplatin powder of the invention are described in more detail.

All individual particles of the fine cisplatin powder of the invention, when observed under an electron microscope at about 1,000 to 4,000×, are in the form of prismatic or plate crystals with a size of 30 μm or less and hardly form large secondarily agglomerated particles.

Figure 2:
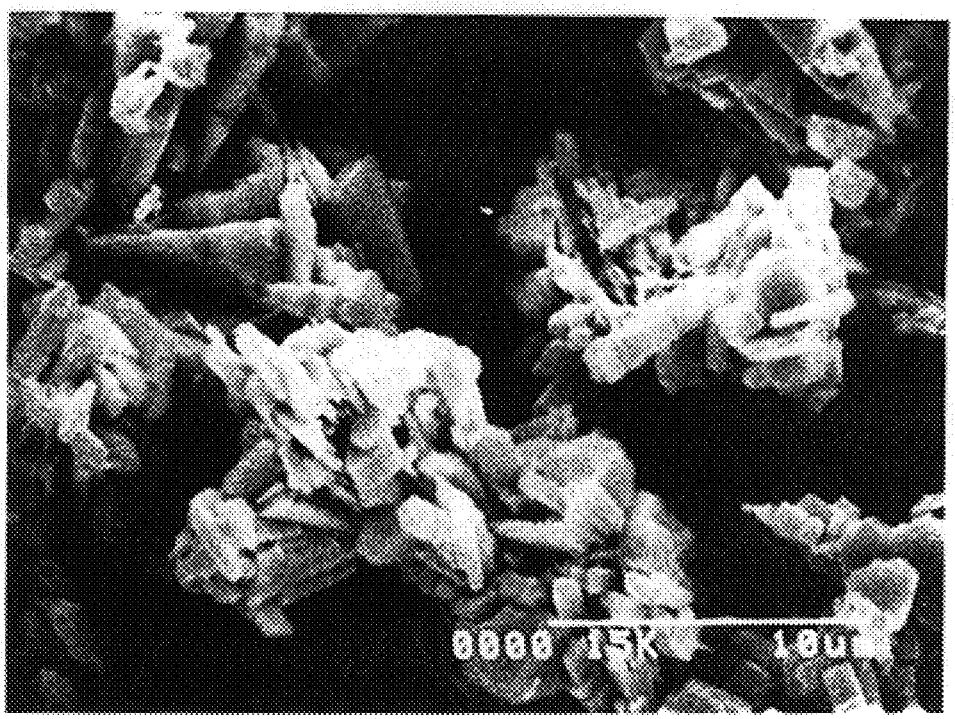
FIG. 2 is an electron microphotograph (4000×) of the fine cisplatin powder obtained in the Comparative Example.

On the other hand, individual particles (Comparative Example) according to the Examples in Japanese Patent Publication No. 13174/1991 described below are as small as 5 μm or less, and these are primarily agglomerated in the form of scales (about 10 μm) and these primarily agglomerated particles are further secondarily agglomerated to form an aggregate. For reference, images of crystals of the fine powders in the invention and in the Comparative Example under an electron microscope are shown in FIG. 1 (the present invention) and FIG. 2 (Comparative Example). Further, in the fine cisplatin powder of the invention, e.g. secondarily agglomerated particles as large as 40 meshes or more account for 10% or less (degree of the particles on a screen in a 40-mesh screen passage test shown in Test Example 2), preferably 1 to 10%, more preferably 1 to 5%. Further, the properties (physical properties) of the fine cisplatin powder of the invention are that the degree of compressibility of the powder derived from a tapping test shown in Test Example 3 is 45 to 54%, preferably 46 to 50%, and the bulk degree is 0.45 to 0.55, preferably 0.48 to 0.53. In addition, when 100 mg of the fine cisplatin powder of the invention and 100 ml physiological saline or distilled water are shaked lightly (2 to 3 r.p.s.) in a test tube, it is completely dissolved within 10 minutes, preferably within 6 minutes, more preferably within 5 minutes, usually for 2 to 5 minutes. By virtue of these properties, the fine powder is easy in the operation of pharmaceutical manufacturing, and the resulting pharmaceutical preparation of the fine powder can be dissolved and used for hepatic intra-arterial injection, and due to good dispersion, for hepatic embolization therapy.

Hereinafter, data obtained from powder X-ray diffractometry (filtered CuKa1 radiation, 1,5406 angstrom) for the crystal structure of the fine cisplatin powder of the invention are shown in Table 1.

Table 1.

Major peaks in an X-ray diffraction profile of the powder of the invention in Example 1

| 2θ | Relative Strength | Spacing (angstrom) |
| --- | --- | --- |
| 13.98 | 100 | 6.329 |
| 15.1 | 22 | 5.862 |
| 16.42 | 24 | 5.394 |
| 24.2 | 8 | 3.674 |
| 26.92 | 24 | 3.309 |
| 28.51 | 12 | 3.128 |

As is evident from the table above, the fine cisplatin powder of the invention is characterized by having strong peaks at 13.98, 15.1, 16.42, and 26.92 as 2θ values.

On the other hand, in an X-ray powder diffraction profile of e.g. a lyophilized product measured under similar conditions, no clear characteristic peaks at the above 2θ values were observed, and its crystal structure was clearly different.

Hereinafter, the effect of the invention is specifically described by reference to suitable comparison with the prior art.

First, the comparison of the degree of a remaining tertiary amide as the solvent for crystallization, such as N,N-dimethylformamide (DMF) indicated that the residual amount of the solvent in the fine cisplatin powder in the prior art (Japanese Patent Publication No. 13174/1991) is 70 ppm or more in analysis by gas chromatography, whereas the residual amount of the solvent in the fine cisplatin powder of the invention is 30 ppm or less (see Test Example 1).

If the fine cisplatin powder with a large amount of residual DMF obtained in the prior art is subjected to the solvent removal step in the present invention to reduce residual DMF, the solvent content is reduced, but its fluidity is worsened, and none of such fine cisplatin powder as in the invention with a less amount of residual DMF and excellent in fluidity etc. cannot be obtained (see the Reference Example).

Then, the powder was vibrated for 5 minutes on a 40-mesh screen and the degree of the powder remaining on the screen was compared for evaluation of powder agglomeration related to the easiness of the operation of pharmaceutical manufacturing. As a result, the powder of the invention was hardly agglomerated and hardly adhered to the screen etc. and almost all of the powder passed through the screen. On the other hand, both the powder obtained in the prior art (Comparative Example) and the powder obtained by reducing the content of the solvent in the powder of the Comparative Example (Reference Example) formed agglomerated particles with larger diameters than the mesh size of the screen, and the majority of the powder remained on the screen (see Test Example 2).

The filling property of the powder is one of important evaluation factor the operation of pharmaceutical manufacturing, and this serves as an indicator of fluidity. Hence, the fine cisplatin powder was accumulated in a measuring cylinder and tapped, and the degree of compressibility and bulk degree, derived from its apparent bulk density and volume, were determined for comparison of filling property. The bulk degree was determined by a method reported by Zairyo, vol. 14, page 574 (1970), specifically by a method described in Test Example 3.

The fine cisplatin powder of the invention was low in both the degree of compressibility and the bulk degree and excellent in filling property.

For examination of solubility, 100 mg of the fine cisplatin powder of the invention was mixed with 100 ml physiological saline and shaked lightly so that it was dissolved within 5 minutes. On the other hand, secondary agglomerated particles not dispersible therein remained in the samples according to the Comparative Example and the Reference Example and these were actually not sufficiently dissolved even after 10 minutes.

Further, the fine cisplatin powder of the invention was very superior in stability during storage, and when sealed in a glass brown vial, it was not decomposed during storage under natural conditions in room even for 39 months.

The fine cisplatin powder provided by the present invention can be used to produce a sterile raw medicine by a germ-removal treatment for and aseptically charged into a sterilized sealed vessel such as ampul or glass vessel whereby a pharmaceutical preparation of the fine cisplatin powder is prepared.

To clarify the advantageous effect of the fine cisplatin powder of the invention, a powder (Comparative Example) according to Example 4 in Japanese Patent Publication No. 13174/1991 and a powder (Reference Example) obtained by further subjecting the powder in said prior art to a solvent (dimethylformamide)-removal treatment (the solvent-removal treatment in the invention) were used.

Hereinafter, the present invention is described in more detail by reference to the Examples, which however are not intended to limit the present invention.

EXAMPLE 1

1080 ml of N,N-dimethylformamide was mixed with 120 ml of 3 N hydrochloric acid. 30.0 g cisplatin was added thereto and dissolved with stirring at room temperature for 1 hour. This solution was passed through a 0.2 μm filter to remove insoluble components. Under stirring and cooling, the cisplatin solution was dropped at a constant rate for 33 minutes into 2400 ml of 0.3 N hydrochloric acid previously cooled at 15° C. A suspension having a fine cisplatin powder precipitated in it was obtained. After dropping was finished, the suspension was stirred at room temperature for 1 hour. The precipitated fine cisplatin powder was collected by filtration and washed twice with 50 ml of 0.1 N hydrochloric acid. The wet cake thus obtained was suspended in 360 ml of 0.1 N hydrochloric acid and stirred at room temperature for 4 hours. This suspension was filtered to give the fine cisplatin powder. It was washed twice with 50 ml of 0.1 N hydrochloric acid and then twice with 50 ml of ethanol. By drying under reduced pressure for 3 hours, 22.55 g fine cisplatin powder was obtained.

100 mg of the resulting fine cisplatin powder and 100 ml physiological saline were mixed in a test tube, and after shaken lightly for 4 minutes, its complete dissolution was confirmed with visual inspection.

EXAMPLE 2

Production of Sterile Raw Medicine of the Fine Cisplatin Powder

The instruments, filter etc. used were those previously sterilized by a suitable sterilization method. 3.6 L of N,N-dimethylformamide and 0.4 L of 3 N hydrochloric acid were mixed. 100 g cisplatin was added thereto and dissolved by stirring at room temperature for 1 hour. This solution was passed through a 0.2 μm membrane filter previously sterilized. Under stirring and cooling, this cisplatin solution was dropped at a constant rate for 25 minutes into 8.0 L of 0.3 N hydrochloric acid kept cold at 15° C. having passed through a 0.2 μm membrane filter previously sterilized. A fine cisplatin powder was precipitated to give a suspension. After dropping was finished, the suspension was stirred at room temperature for 1 hour. The precipitated fine cisplatin powder was collected by filtration and washed twice with 180 ml of 0.1 N hydrochloric acid previously sterilized by filtration. The resulting wet cake was suspended in 1.2 L of 0.1 N hydrochloric acid previously sterilized by filtration, and stirred at room temperature for 4 hours. This suspension was filtered to give the fine cisplatin powder. It was washed twice with 180 ml of 0.1 N hydrochloric acid and then twice with 180 ml ethanol sterilized by filtration. It was dried for 3 hours under reduced pressure to give 65.1 g fine cisplatin powder. The powder was introduced into a sterilized glass vessel and sealed.

100 mg of the resulting fine cisplatin powder and 100 ml physiological saline were put in a test tube, mixed and lightly shaken for 5 minutes, and after shaking, its complete dissolution was confirmed with visual inspection.

Comparative Example 20 g cisplatin was dissolved in 500 ml of DMF-conc. HCl (9:1). This solution was stirred for 1 hour, and 1000 ml of 0.1 N HCl was added thereto. The resulting suspension was stirred for 15 minutes and solids were recovered by filtration. These solids were washed twice with 40 ml of 0.1 N HCl and twice with 80 ml acetone and dried under reduced pressure at room temperature for 3 hours to give a powder.

Reference Example

The fine cisplatin powder obtained in Comparative Example 1 was subjected to stirring treatment in 0.1 N HCl at room temperature for 4 hours to remove DMF according to Example 1 of the present invention, whereby a powder was obtained.

Test Example 1

Analysis of the Amount of Residual DMF

The fine cisplatin powder obtained in each of the above processes was dissolved in dimethylsulfoxide and analyzed by gas chromatography to quantify the residual DMF contained in the product.

Residual DMF in the fine cisplatin powder in Example 1 according to the present invention: 18 ppm.

Residual DMF in the fine cisplatin powder in the Comparative Example: 72 ppm.

Residual DMF in the fine cisplatin powder in the Reference Example: 27 ppm.

Conditions for analysis by gas chromatography

Column: Gas-Chro Pack 55 (GL Science Co., Ltd.).
Column temperature: 180° C.
Carrier gas: nitrogen, 50 ml/min.
Detector: Hydrogen flame ionization detector.
Sample: 0.2 g sample is dissolved in dimethylsulfoxide to give 1 ml solution, and 5.0 μl is injected.

Test Example 2

Sieve Analysis 2.00 g of cisplatin, which was in a disintegrated form by passing it through a 40-mesh screen, was placed quietly on a 40-mesh screen with an outer diameter of 7.5 cm, and it was vibrated (in a vertical direction) with 50 times of vibration/sec. and a vibration strength of 4.6 G for 5 minutes in a screen vibrator. The strength of vibration was measured in "strain gauge-type acceleration converter". The amount of the cisplatin having passed through the screen and the amount thereof remaining on the screen were measured to determine the residual degree.

The fine cisplatin powder of the invention in Example 1. The residual degree: 2.0%.

The fine cisplatin powder in the Comparative Example, the residual degree: 63.5%.

The fine cisplatin powder in the Reference Example. The residual degree: 70.0%.

The residual degree on the screen in the sieve analysis was determined by the following formula described in general test methods according to the Japanese Pharmacopoeia:

A=B/S×100

A: Residual degree (%)
B: Sample remaining on the screen (g)
S: Sample (g)

Test Example 3

Filling Test by Tapping

The fine cisplatin powder having passed through a 40-mesh screen was introduced quietly via a powder funnel into a 25-ml measuring cylinder and accumulated in an volume of 20 to 25 ml. The apparent volume in a loosely filled state was measured. It was tapped with a tap height of 2 cm. The apparent volume every 20 times of tapping was measured. When the apparent volume became constant, tapping was finished. The charged cisplatin was weighed, and its bulk density after each tapping was determined. The degree of compressibility was derived from this bulk density. Further, the bulk degree was determined by a method reported in Zairyou, Vol. 14, page 574 (1970). The fine cisplatin powder of the invention in Example 1. The degree of compressibility of the charged powder: 48.8%. The bulk degree: 0.51.

The fine cisplatin powder according to the Reference Example. The degree of compressibility of the charged powder: 58.6%. The bulk degree: 0.65.

The degree of compressibility derived from the tapping test is obtained from the following equation:

c=(ρf−ρ0)/ρf×100 c: degree of compressibility (%)
ρf: tight bulk density (g/ml)
ρ0: loose bulk density (g/ml)

The bulk degree can be derived in the following method.

When the relationship between n/C and n is plotted from data obtained from the above tapping filling, N: tapping number (times)
C=1−v/v0 (V0: apparent volume in a loosely filled state, V: apparent volume after each tapping),
the linear relationship between n/C and n is obtained and corresponds to the primary formula: n/C=1/ab+n/a (a, b: constant) and from the inclination of the graph, the bulk degree: a is derived.

Test Example 4

Storage Stability Test 15 g of the fine cisplatin powder of the invention was sealed in a transparent glass vial and stored for 39 months under natural conditions in a room. As a result of the measurement of the degree of decomposition thereafter by HPLC, none of cisplatin analogues formed by decomposition were observed, and the content of the raw medicine of cisplatin was 100.1%.

Comparison with the Conventional Method in the Operation of Pharmaceutical Manufacturing The fine cisplatin powder of the invention (Example 1) did not cause secondary agglomeration, was smooth and highly fluidic and did not adhere to a vessel, and the process proceeded smoothly in the various procedures of pharmaceutical manufacturing (storage, mixing, dispensing and packaging, weighing etc.). On the other hand, the fine cisplatin powders according to the Comparative Example and Reference Example were in a massive material after drying, so grinding with a mill was required, and a chemical hazard caused by scattering of the fine powder is inevitable unless the process is conducted in a closed system. Further, the powder after ground with a mill caused secondary agglomeration, was poor in fluidity, adhered to instruments etc., caused obstacles to the operation of mixing, dispensing, packaging and weighing in the process of pharmaceutical manufacturing, while accurate weighting etc. were difficult.

INDUSTRIAL APPLICABILITY

The present invention relates to a pharmaceutical preparation of fine cisplatin powder provided as an anticancer agent for intra-arterial injection therapy in cancer therapy, which is highly fluidic and easily handled in the operation of pharmaceutical manufacturing. Further, it is excellent in dispersion, is rapidly dissolved in water and can thus provide a highly convenient fine powder preparation. Further, a fine cisplatin powder applicable clinically and safely with a less content of N,N-dimethylformamide can be provided.

What is claimed is:

1. A fine cisplatin powder consisting essentially of a fine cisplatin powder passing through a 40-mesh screen, wherein when a fine powder consisting of finely divided particles is placed on a 40-mesh screen and subjected to a screen passage test under vibration at 50 r.p.s. for 5 minutes with a vibration strength of 4.6 G, the percentage of the secondarily agglomerated particles remaining on the screen is 10% or less, and the fine powder is in a crystal form having the following characteristic peaks in an X-ray powder diffraction pattern:

| 2θ | Spacing (angstrom) |
|---|---|
| 13.98 | 6.329 |
| 15.1 | 5.862 |
| 16.42 | 5.394 |
| 26.92 | 3.309 | and in the form of prismatic or plate crystals with a size of 30 μm or less.

2. A fine cisplatin powder according to claim 1, wherein the degree of compressibility of the powder derived from a tapping test is 45 to 54%, the bulk degree is 0.45 to 0.55, and the content of a tertiary amide is 60 ppm or less.

3. A find cisplatin powder according to claim 1 or 2, wherein the dissolution time is within 10 minutes by slight shaking at a condition of 2 to 3 r.p.s. to give an aqueous solution of cisplatin at a concentration of 1 mg/ml.

4. A fine cisplatin powder according to claim 3, wherein said fine cisplatin powder is used for intra-arterial injection therapy or for embolization therapy in cancer therapy.

5. A process for the production of a fine cisplatin powder, comprising the following successive steps:

(1) preparing a cisplatin solution containing hydrogen chloride at a concentration of 0.3 to 3% by weight, water at 4% by weight to 15% by weight and cisplatin at a concentration of 20 to 40 g/L in a tertiary amide solution, (2) dropping said cisplatin solution at a constant rate for 20 to 40 minutes to 1- to 4-fold excess volume of 0.2 to 2 N hydrochloric acid kept cold at 10 to 30° C. under stirring to precipitate a find cisplatin powder, and (3) recovering the precipitated fine cisplatin powder by filtration.

* * * * *